United States Patent [19]

Awano et al.

[11] Patent Number: 4,977,658
[45] Date of Patent: Dec. 18, 1990

[54] SENSOR AND METHOD FOR THE PRODUCTION THEREOF

[75] Inventors: Hiroshi Awano, Yonezawa; Yuka Kawabata, Yokohama; Takayoshi Iwai, Yokosuka, all of Japan

[73] Assignee: Kabushiki Kaisha Toshiba, Kanagawa, Japan

[21] Appl. No.: 264,663

[22] Filed: Oct. 31, 1988

[30] Foreign Application Priority Data

Oct. 31, 1987 [JP] Japan .............................. 62-276806

[51] Int. Cl.⁵ .......................... G01R 3/00; H01S 43/00
[52] U.S. Cl. ................................ 29/25.01; 73/23.200; 427/226
[58] Field of Search ................... 427/126.2, 126.3, 226, 427/419.3; 29/592.1, 610.1, 825, 846; 73/23; 338/34; 437/8, 245

[56] References Cited

U.S. PATENT DOCUMENTS

| | | | |
|---|---|---|---|
| 3,522,075 | 7/1970 | Kiel | 327/226 |
| 4,332,879 | 1/1982 | Pastor et al. | 437/245 |
| 4,569,826 | 2/1986 | Shiratori et al. | |
| 4,656,455 | 4/1987 | Tanino et al. | 427/126.3 |
| 4,740,387 | 4/1988 | Manaka | 427/226 |
| 4,752,501 | 6/1988 | Hicks et al. | 427/226 |

OTHER PUBLICATIONS

Solid State Technology, entitled "Electrical Applications of Thin-Films Produced by Metallo-Organic Deposition," by C. Y. Kuo, dated Feb. 1974, pp. 49-55.
Denshi Zairyo, by Y. Nakamura, dated May 1982, pp. 51-54.

*Primary Examiner*—Hezron E. Williams
*Attorney, Agent, or Firm*—Finnegan, Henderson, Farabow, Garrett and Dunner

[57] ABSTRACT

Disclosed is a sensor comprising an insulating substrate, a plurality of electrodes coated on the insulating substrate and formed of a thin film conductor of a metallo-organic compound obtained by a pyrolysis, and a layer formed across the electrodes. The layer formed across the electodes has an electrical property changeable in accordance with an atmosphere. The sensor reduces the affection due to the existence of the step portion, restrains the structural deficiency at the step portion and improves the stability of the change with age. By the metallo-organic compound, the thin film layer can be formed by a pyrolysis at relatively low temperatures, and the electrodes can be formed in various structures and by various producing processes.

3 Claims, 2 Drawing Sheets

4,977,658

SENSOR AND METHOD FOR THE PRODUCTION THEREOF

The present application claims priority of Japanese Patent Application No. 62-276806 filed on Oct. 31, 1987.

FIELD OF THE INVENTION AND RELATED ART STATEMENT

The present invention relates to a sensor for detecting temperatures, humidity and gas concentrations present in the atmosphere.

Generally, the sensor for detecting temperatures, humidity and gas concentrations in the atmosphere is provided with a plurality of opposed electrodes formed on an insulating substrate and a sensitive layer made of a material having an electrical property changeable in accordance with the atmosphere formed across the electrodes.

As a method for the production of such sensitive layer on the electrodes, a vapor deposition method, such as vacuum deposition and sputtering, and a screen printing method using a paste have been known.

By the vapor deposition method, it can be obtained a thin layer with precise patterns, a high purity, and an excellent reproductivity and mass-productivity. However, this method has disavantages that it requires a high price apparatus and lacks an adaptability for mass-production.

For solving the disadvantages mentioned above, the screen printing method has been noticed for the production of the sensitive layer and the electrodes, which method requires an apparatus in low cost and an easy operation. Therefore, the method for the production of a gas sensor having such sensitive layer and electrodes obtained by a screen printing method has been proposed.

FIG. 5 is a schematic cross sectional view illustrating such conventional gas sensor, in which opposed electrodes 2 formed by a thick film method in a specific pattern are provided on a ceramic insulating substrate, and a tin oxide semiconductor layer 3 is formed thereon by means of screen printing. And a catalyst layer 4 is formed on the tin oxide semiconductor layer 3 to enhance its sensitivity. A heating element 5 is formed on the back side of the insulating substrate 1 to increase its sensitivity and response characteristics.

In such a gas sensor as described above, the tin oxide semiconductor layer 3 is a thin layer having 1 $\mu$m in thickness and is formed by printing a paste containing a tin organic compound (a kind of metallo-organic compound containing tin) in a specific pattern and by a pyrolysis. However, since the electrodes 2 are obtained by printing and firing a thick film conductive paste (for example, the gold paste #8880, product of ESL company), it has 10 to 20 $\mu$m in thickness.

As mentioned above, since the conventional gas sensor is formed such that the thickness of the electrodes 2 is remarkably thicker than that of the tin oxide semiconductor layer 3, cracks are caused in the step portion A of semiconductor layer 3.

Such structural drawbacks as mentioned above causes an increase of the electrical resistance, an acceleration of change with age due to the interaction between the defective portion and the atmosphere, and a decrease of reliability.

To avoid the above problems, it can be considered to form the electrodes 2 on the tin oxide semiconductor layer 3. However, the tin oxide semiconductor layer 3 is normally fired at a temperature in the range of 400° to 600° C., while the thick film conductive paste for the electrodes 2 is fired at a temperature of not less than 800° C. in general (when gold paste #8880 is used, it was fired at a temperature in the range of 900° to 1,000° C.). Therefore, in view of the temperature of process, forming the electrodes 2 by printing and firing is impossible after the tin oxide semiconductor layer 3 is formed.

The above problems corresponding to the sensor for sensing the atmosphere are not limited in the case of the gas sensor.

As mentioned above, in the conventional atmosphere sensor, since the electrodes are formed on the insulating substrate by printing and firing a thick film conductive paste, the sensitive layer formed thereon is affected by the step portion A and caused a structural deficiency, and accelerates the change with age. Further, even if the electrodes are formed on the sensitive layer to avoid the problems as above, the previously formed sensitive layer will be damaged, because a temperature for firing the electrodes is higher than that of the sensitive layer.

OBJECT AND SUMMARY OF THE INVENTION

The present invention has been made under circumstances as described above, and the object of the present invention is to provide a sensor in which a potential deficiency of a sensitive layer is reduced, and has an increased stability of change with age and improved processibility of forming a plurality of electrodes.

The sensor of the present invention comprises an insulating substrate, a plurality of electrodes coated on the insulating substrate and formed of a thin film conductor of a metallo-organic compound obtained by a pyrolysis, and a layer formed across the electrodes, which the layer has an electrical property changeable in accordance with an atmosphere.

In the sensor of the present invention, since a thin film conductor formed by a pyrolysis of a metallo-organic compound coated on the insulating substrate is used for the electrodes, the affection against the sensitive layer caused by the step portion is reduced, the structural deficiency of the layer at the step portion is restrained and the stability of the change with age is increased. Further, since the metallo-organic compound is fired at relatively lower temperatures, the electrodes can be formed on the sensitive layer by printing and firing without damaging the surface of the sensitive layer.

DETAILED DESCRIPTION OF THE PREFERRED EMBODIMENT

Now, the present invention will be described in detail with reference to the accompanying drawings. In addition, the detailed description regarding under mentioned metallo-organic compound has been written in "SOLID STATE TECHNOLOGY/February 1974" on page 49, lines 8 through 10 in the right column, i.e., in the metallo-organic, the metal atom is linked to an oxygen, a sulfur, a nitrogen or a phosphorus atom which in turn is attached to one or more carbon atoms.

Figure 1:
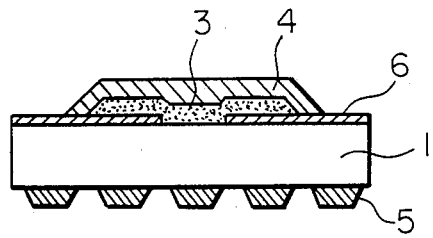
FIG. 1 is a cross sectional view illustrating an embodiment of a gas sensor of the present invention.

FIG. 1 shows an embodiment of a gas sensor of the present invention using a metal oxide semiconductor. Electrodes 6 formed of a thin film conductor obtained by a pyrolysis of a metallo-organic compound are provided on the surface of a ceramic insulating substrate 1 made of such as alumina. A tin oxide semiconductor layer 3 is formed across the electrodes 6, and a catalyst layer 4 is formed thereon. Further, a heating element 5 formed of a thick film containing platinum is provided on the back side of the insulating substrate 1.

The gas sensor of this embodiment is produced as follows.

First, the heating element 5 formed of a thick film containing platinum is formed on the back side of the ceramic insulating substrate 1 made of such as alumina, then the electrodes 6 are printed on the surface of the substrate 1, a metallo-organic compound, whose coupling atom is gold such as the paste containing gold mercaptide (contained gold is 18%,) is coated in a specific pattern. Since this paste is a homogeneous solution having viscosity, it can be obtained the thin layer having homogeneity and smooth surface as compared with the conventional thick film paste. Then, it is fired at about 600° C. to obtain the electrodes 6 having the thickness of 0.5 μm.

On the electrodes 6, a paste containing a metallo-organic compound, whose coupling atom is tin (such as the paste containing tin-2ethylhexanoate), is printed in a specific pattern, and is pyrolyzed at 600° C. to obtain a tin oxide semiconductor layer 3 having the thickness of about 1 μm. Further, a catalyst layer 4 having alumina and platinum is formed by printing.

In this embodiment, the electrodes 6 are fired at 600° C., it is also possible to fire the paste sufficiently at 500° C. Furthermore, as the metallo-organic compound, there can be cited some of other compound which can be fired at about 300° C. in accordance with its kinds. In addition, platinum can be used as the main component of the electrodes 6.

Figure 2:
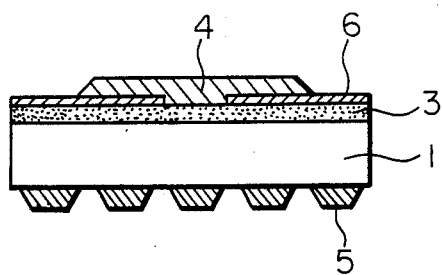
FIG. 2 is a cross sectional view illustrating other embodiment of the present invention.

FIG. 2 shows the other embodiment of the present invention, in which the electrodes 6 are formed on a tin oxide semiconductor layer 3. In the sensor of this embodiment, since the firing temperature for the electrodes 6 is lower than that of the tin oxide semiconductor layer 3, the tin oxide semiconductor layer 3 is not damaged during firing the electrodes 6.

Figure 3:
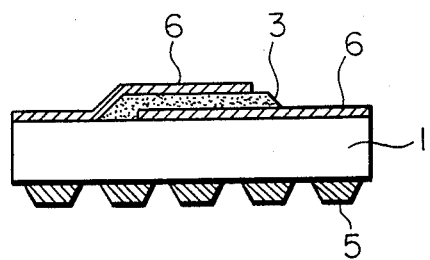
FIG. 3 is a cross sectional view illustrating another embodiment of the present invention.

FIG. 3 shows another embodiment of the present invention. The sensor has a sandwiched structure in which a tin oxide semiconductor layer 3 is provided within two sheets of the electrodes 6.

The sensor of this embodiment has the same reason as above, that the tin oxide semiconductor layer 3 is not damaged during firing the electrodes 6.

Figure 4:
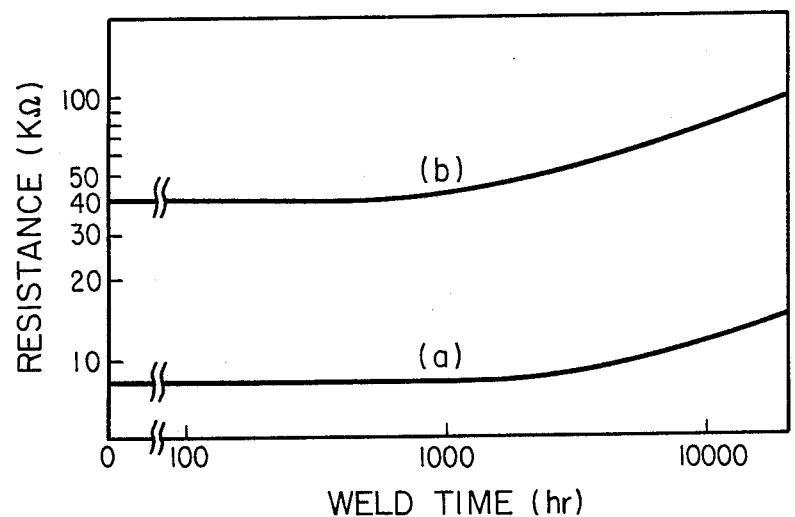
FIG. 4 is a graph showing the resistance changes between the gas sensor of the present invention and the conventional gas sensor.
Figure 5:
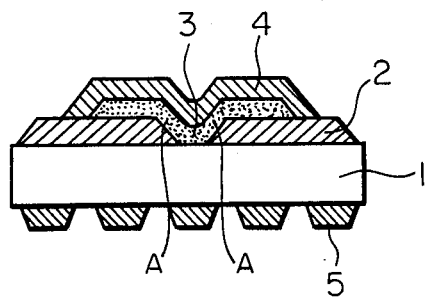
FIG. 5 is a cross sectional view illustrating the conventional gas sensor.

FIG. 4 is a graph showing the change with age of the resistance values of the semiconductor in the embodiment shown in FIG. 1 and the conventional gas sensor (comparative embodiment).

In the gas sensor using a metal oxide, initially it shows a rapid change with age in general and then it is gradually transferred to a slow change. Accordingly, when plotting the relation between resistance and time in a logarithm, it is shown many cases where the curve may at some point rise or down. Therefore, the timing at which the curve is transferred in upward or downward is deemed as a criterion showing the stability of the change with age.

As shown in FIG. 4, in the sensor of the embodiment, an increase of the resistance value starts about in 2,000 hours and it becomes two times about in 30,000 hours. On the contrary, in the comparative example formed in such way that the electrodes are formed by the thick film, the increase of the resistance value starts about in 500 hours and it becomes instantly two times about in 10,000 hours. Further, in spite of the same forming conditions under which a semiconductor layer and a catalyst layer are formed on the electrodes, it is seen that the resistance value of the gas sensor of the embodiment is extremely lower than that of the comparative embodiment.

As described above, by the present invention, it is possible not only to lower the resistance value but also to improve the stability of the change with age. This is considered due to the fact that the semiconductor layer having the step portion has the large deficiency of the layer structure in proportion to the size of the step portion.

Actually, from the observation through a scanning electron microscope, it is observed that the semiconductor layer of the embodiment has an excellent layer without drawbacks, while the layer of the comparative embodiment has many cracks at the step portion.

What is explained above is the case in which the sensitive layer of the sensor is made of a metal oxide semiconductor, while, even if the sensitive layer is an organic compound, provided that it is a compound having good heat-resistance such as phthalocyanine or derivatives thereof or metal complexes thereof, it is possible to form the electrodes on the sensitive layer.

Furthermore, in the case that the sensitive layer is not a semiconductor but a dielectric, the sandwiched type of structure where the sensitive layer is positioned between two sheets of the electrodes is required in most cases as shown in FIG. 3. The present invention can be applied as well, because the electrodes can be formed on the sensitive layer without being damaged.

Finally, the thin film conductor has an excellent adhesion property to the substrate, in addition, it is a paste consisting of a homogeneous solution having viscosity, so that it has in most cases an excellent adhesion property as compared with the thick film.

As mentioned above, in the present inventon, the electrodes are formed by a thin film conductor which is formed by printing and firing the paste containing a metallo-organic compound, so that the affection of the step portion against the sensitive layer is restrained and improvements of the stability of the change with age and the reliability of the sensor are obtained. Further, since the metallo-organic compound is able to be fired at relatively low temperature, the electrodes are formed on the sensitive layer without being damaged, and it is possible to provide the sensor easily and in low cost.

What is claimed is:

1. A method for the production of a sensor, comprising the steps of:
   forming a plurality of electrodes spaced a distance from one another on an insulating substrate, said electrodes being formed of a thin film conductor of a metallo-organic compound obtained by a pyrolysis at approximately 600° C., said electrodes having a thickness of approximately 0.5 μm; and forming a semiconductor layer on said electrodes and across said distance, said semiconductor layer being in contact with said insulating substrate and having an electrical property changeable in accordance with an atmosphere.

2. A method for the production of a sensor, comprising the steps of:

coating and forming a semiconductor layer having a thickness of approximately 1 μm on an insulating substrate, said semiconductor layer having electrical property changeable in accordance with an atmosphere; and forming a plurality of electrodes on said semiconductor layer in a spaced manner, said electrodes being formed of a thin film conductor of a metallo-organic compound obtained by pyrolysis at approximately 600 ° C. and having a thickness of approximately 0.5 μm.

3. A method for the production of a sensor, comprising the steps of:

forming a first electrode on a substantial portion of an insulating substrate, the first electrode is formed of a thin film conductor of a metallo-organic compound obtained by a pyrolysis;

coating a semiconductor layer on the first electrode and on said insulating substrate, said semiconductor layer having electrical property changeable in accordance with an atmosphere and having a thickness of approximately 1 μm; and forming a second electrode on said coating layer to oppose the first electrode and on said insulating substrate, the second electrode is formed of a thin film conductor of a metallo-organic compound obtained by pyrolysis at approximately 600° C., said first and second electrodes each having a thickness of approximately 0.5 μm.

* * * * *